United States Patent [19]

Dietsche et al.

[11] 4,227,001
[45] Oct. 7, 1980

[54] PREPARATION OF POLYCHLORINATED PYRIDINES FROM 2,4-DICHLORO-6-(TRICHLORO METHYL)PYRIDINE

[75] Inventors: Thomas J. Dietsche, Berkeley; Jim Love, Walnut Creek, both of Calif.

[73] Assignee: The Dow Chemical Company, Midland, Mich.

[21] Appl. No.: 16,631

[22] Filed: Mar. 1, 1979

Related U.S. Application Data

[63] Continuation-in-part of Ser. No. 916,450, Jun. 19, 1978, abandoned.

[51] Int. Cl.³ .......................................... C07D 213/26
[52] U.S. Cl. .................................................... 546/345
[58] Field of Search ........................................ 546/345

[56] References Cited

U.S. PATENT DOCUMENTS

| | | | |
|---|---|---|---|
| 3,418,323 | 12/1968 | Johnston et al. | 546/345 |
| 3,538,100 | 11/1970 | Smith | 546/345 |
| 3,732,230 | 5/1973 | Brewer et al. | 546/180 |

FOREIGN PATENT DOCUMENTS 957276  5/1964  United Kingdom ..................... 546/345

*Primary Examiner*—Alan L. Rotman
*Attorney, Agent, or Firm*—J. W. Ambrosius

[57] ABSTRACT

Pentachloropyridine and polychloro derivatives of 2-(trichloromethyl)pyridine are prepared by reacting 2,4-dichloro-6-(trichloromethyl)pyridine in the liquid state with chlorine at temperatures of from about 160° C. in the presence of an amount of catalyst effective to catalyze the reaction.

14 Claims, No Drawings

PREPARATION OF POLYCHLORINATED PYRIDINES FROM 2,4-DICHLORO-6-(TRICHLOROMETHYL)PYRIDINE

CROSS-REFERENCE TO RELATED APPLICATION

This application is a continuation-in-part of our co-pending application Ser. No. 916,450, now abandoned filed June 19, 1978.

BACKGROUND OF THE INVENTION

The present invention concerns the preparation of pentachloropyridine and polychloro pyridines such as 2,3,4-trichloro-,2,4,5-trichloro- and 2,3,4,5-tetrachloro-6-(trichloromethyl)pyridine.

The chlorinated pyridine derivatives of the present invention are known compounds having been previously prepared by a number of processes. These compounds have uses such as herbicides, pesticides, etc., and are also employed as chemical intermediates in the preparation of other highly desired herbicide or pesticide products. Previous methods for preparing such compounds include those described in U.S. Pat. Nos. 3,538,100 and 3,186,994 and the prior art noted therein. Thus, according to the 3,538,100 patent, pentachloropyridine (hereinafter referred to for convenience as "penta") has been prepared by chlorination of liquid 2,6-dichloropyridine at temperatures of at least about 180° C. and in the presence of a metallic halide catalyst. Polychloropyridines, including penta, are also produced according to the 3,186,994 patent by chlorinating a polychloro-(trichloromethyl)-pyridine reactant in the liquid state at a temperature of at least 160° C., preferably under irradiation with ultraviolet light.

SUMMARY OF THE INVENTION

According to the present invention, it has been discovered that chlorinated pyridine compounds selected from the group consisting of pentachloropyridine, 2,3,4-trichloro-,2,4,5-trichloro- and 2,3,4,5-tetrachloro-6-(trichloromethyl)pyridine can be obtained in a process which comprises contacting liquid 2,4-dichloro-6-(trichloromethyl)pyridine with chlorine at temperatures of from about 160° C. in the presence of an amount of catalyst effective to catalyze the reaction. The reaction can be practised to convert most or all of the 2,4-dichloro-6-(trichloromethyl)pyridine to pentachloropyridine, e.g., convert the trichloromethyl radical to a chloro radical with accompanying replacement of hydrogen on the ring, or to obtain optimum amounts of the polychloro derivatives of (trichloromethyl)pyridine. The process can also be carried out to provide mixtures of said products which can be separated from each other. The process is preferably carried out under anhydrous conditions. Use of the 2,4-dichloro- and 2,3,4-trichloro- and/or 2,4,5-trichloro-6-(trichloromethyl)pyridine derivatives or mixtures thereof as starting materials also forms a part of the invention.

DETAILED DESCRIPTION OF THE INVENTION

The process of the present invention is carried out by preferably using 2,4-dichloro-6-(trichloromethyl)pyridine as the starting material, although mixtures of the same with the trichloro derivatives, or one of the trichloro derivatives alone can be used as a starting reactant to prepare 2,3,4,5-tetrachloro-6-(trichloromethyl)pyridine and/or pentachloropyridine. The invention, in its broadest aspect, thus comprises contacting a starting material of the formula:

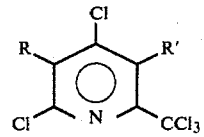

wherein R and R' are each independently chloro or H, with the proviso that at least one of R and R' is always H, in the liquid phase with chlorine at a temperature of at least about 160° C. and in the presence of a catalyst effective to catalyze the reaction. Preferably, a starting material wherein R and R' are both H is employed. In another embodiment, a starting material wherein R is chloro and R' is H is preferably employed. In still another embodiment, a starting material wherein R is H and R' is chloro is preferred. In a further embodiment, the starting material preferably comprises a mixture of the compounds encompassed by the above formula.

In carrying out the process of the present invention, gaseous chlorine is contacted with a liquid starting material at a temperature of at least about 160° C. in the presence of a selected catalyst. Atmospheric or superatmospheric pressures can be employed.

An equimolar amount of the chloride gas reactant is employed with from about 0.3 to about 10 excess molar proportions of chlorine per mole of starting material desirably being employed. The continuous passage of excess chlorine gas through the reaction mixture serves not only to supply a large amount of reactant but to sweep out any carbon tetrachloride or hydrogen chloride by-products. The most suitable rate at which the chlorine gas is fed will vary with the reaction temperature, pressure, reaction mixture volume, end-product desired, etc. An excess amount of from about 0.3 to about 5.0 moles of chlorine per hour is usually employed per mole of starting material.

A catalyst and amount thereof effective to catalyze the reaction with chlorine is required to obtain the products of the present invention and any catalyst which is thus effective and compatible with the process is considered to be within the scope of the present invention. Catalysts which are ineffective in so catalyzing the reaction are, of course, not within the scope of the invention. Representative catalyst include, for example, Lewis acid type catalysts such as metals, metaloxyhalides or metallic halides capable of being converted to covalent metallic chlorides under the conditions of the chlorination reaction of the present invention, as well as non-metal catalysts, such as, for example, tellurium tetrachloride. While tellurium is a non-metal element, those skilled in the art recognize it possesses properties and characteristics of many metals. Metals themselves such as iron, zinc, aluminum, tantalum, and the like can be employed, preferably in the powdered form. Representative covalent metallic chlorides and/or metallic oxychlorides and/or halides which can be converted to the chloride form include those such as ferric chloride, ferric bromide, aluminum chloride, aluminum bromide, antimony pentachloride, molybdenum tri- or pentachloride or oxytetrachloride, tungsten hexachloride, boron trifluoride, titanic chloride, nickel chloride, zinc chloride, tantalum pentachloride, ruthenium trichloride, niobium pentachloride, copper chloride, chromium trichloride, vanadium trichloride, cobalt chloride, and similar materials.

As will be understood by those skilled in the art, no equivalency in activity or operability of the catalyst materials is to be inferred. While certain catalysts have been found to provide good results over a short reaction period, for example, at atmospheric pressure, others which may be operable may require long reaction time periods which may not be economically feasible to obtain similar results. Further, certain catalysts may be superior when employed at elevated temperatures and/or temperatures. The degree of catalytic activity may also vary depending upon the particular product which is to be produced, the degree of catalyst solubility or miscibility with the starting material, the use of fixed bed versus slurried catalysts, etc. In any event, those skilled in the art can, by routine experimentation according to the teachings of the specification and numerous examples herein, readily determine the optimum catalyst and amount thereof required for any particular product to be made or for any particular set of pressure, temperature or time conditions desired.

Catalysts bonded to inert supports or the use of co-catalysts are also contemplated for use in the present invention. Catalysts preferred for use in the present invention include Lewis acid catalysts. Specific preferred catalysts include ruthenium, tantalum, tungsten, molybdenum, niobium, aluminum, zinc and iron metals or their halides. Highly preferred catalysts for use in the present invention include the ferric and aluminum halides, and iron and aluminum metals. A preferred catalyst is ferric chloride. A preferred class of catalysts include those which are soluble or readily dispersible in the molten starting material. The catalysts must be employed in an amount effective to catalyze the reaction, e.g., a catalytic amount, and are usually employed in an amount ranging from about 0.5 to about 20 mole % based on the amount of chloro-substituted 6-(trichloromethyl)pyridine starting material. Preferably, a catalyst concentration of from about 1.0 to about 10 mole % is employed.

In a preferred method for carrying out the process of the present invention, 2,4-dichloro-6-(trichloromethyl)-pyridine starting material in liquid, e.g., molten form is added to a reactor previously heated to at least about 100° C. and the reactor purged with nitrogen. An effective catalyst in an amount sufficient to catalyze the reaction is then added and chlorine flow commenced at a sufficient rate to pressure the reactor, usually to about 15 psig, or more. The temperature of the reactor is then slowly increased to at least about 160° C. or more and the reaction maintain until sufficient amounts of the desired pyridine compounds are obtained. Liquid samples from the reactor and vent gases are periodically taken and analyzed by known methods to monitor the course of the reaction. The reaction is terminated by stopping the heating of the reactor and the flow of chlorine thereto and allowing the reactor pressure to drop to atmospheric. Distillation of the reaction product obtained can then be carried out to obtain the desirable products therefrom and the still bottoms can be recovered and re-used.

The reaction process starting with 2,4-dichloro-6-(trichloromethyl)pyridine is generally illustrated as follows:

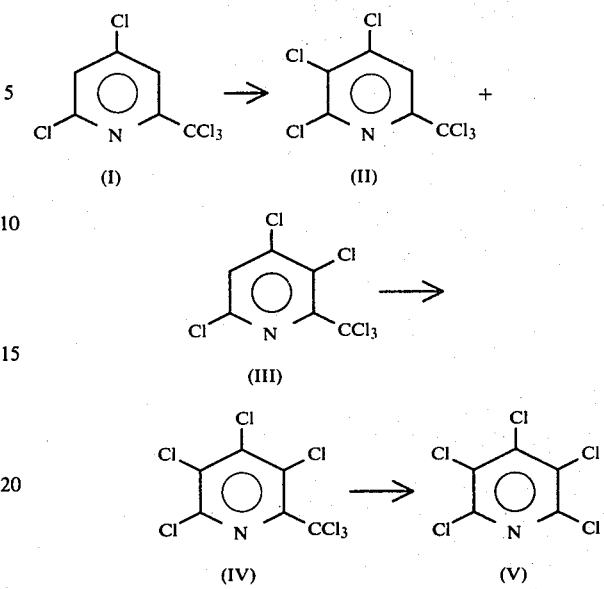

During the initial stage of the reaction sequence the 2,4-dichloro-6-(trichloromethyl)pyridine starting material (I) is largely converted to the 2,3,4-trichloro-6-(trichloromethyl)pyridine (II), with lesser amounts of the 2,4,5-trichloro-6-(trichloromethyl)pyridine (III) and some small amounts of 2,3,4,5-tetrachlor-6-(trichloromethyl)pyridine (IV) and pentachloropyridine (V) being formed. As the reaction continues, products (II) and (III) reach optimum amounts and then begin to decrease as the levels of (IV) and (V) continue to increase. If the reaction sequence is continued for a long enough period, a product comprising (V) as the chief or primary product can be obtained. The course of the reaction can, of course, be monitored and the reaction sequence stopped whenever optimum amounts of one or more of the desired products have been obtained.

In a preferred embodiment, the starting material is (I) and the process is selectively practiced to produce a mixture of chlorinated pyridine compounds comprising product (II) as the primary or chief component of the mixture. In one embodiment wherein (I) is the starting material, the process is selectively practised to obtain (IV) as the primary or chief product contained in the mixture. In still another embodiment using (I) as the starting material, the process is selectively practised to obtain (V) as the primary or chief product of the mixture. In a further preferred embodiment, (II) is the starting material.

While the process of the present invention can be conducted at atmospheric pressure, it is usually advantageous to employ at least slightly increased pressures. Thus pressures of from about 15 psig to about 220 psig or more are preferably employed. In all embodiments of the invention, the only constraint placed upon the superatmospheric pressures employed is one of economics and pressures in excess of 220 psig may be employed, however, those skilled in the art will recognize that the cost factor for pressure equipment to allow operation above 200-220 psig is greatly increased and that the additional cost may exceed any benefits obtained. In a preferred embodiment, the process is carried out at temperatures of from about 160° to about 220° C. and pressures of from atmospheric to about 220 psig, and in the presence of from about 1 to about 10 mole % of a catalyst based on the weight of starting material. In another preferred embodiment, the process of the present invention is carried out at temperatures of from about 190° to about 220° C., at pressures of from about 190 to about 220 psig and in the presence of from about 1 to about 10 mole % catalyst.

The 2,4-dichloro-6-(trichloromethyl)pyridine starting material is known and can be obtained from methods known in the art. The products (II)–(V) likewise are known in the art as are their physical properties.

The following examples illustrate the process of the present invention but are not to be construed as limiting the same. The analysis of the reaction mixtures was accomplished by vapor phase chromatography. The product distribution in all tables is in terms of area percent.

EXAMPLE 1

A chlorination reactor comprising a 300 ml flask fitted with a sparge tube connected via a rotormeter and needle valve to a chlorine source and a condensor connected to a caustic scrubber was charged with a melt of a 2,4-dichloro-6-(trichloromethyl)pyridine (98.2%) starting material. The reaction mixture was then heated at about 200° C. at atmospheric pressure with stirring and chlorine was sparged into the solution at the rate of about 0.1 mole/hr. Samples were removed via a sampling port at various intervals. The reaction was conducted for a period of about 8 hours, with samples being taken at the second, fourth and eighth hour intervals. Analysis of the samples indicated the starting material remained unchanged. At the end of 8 hours, 5 mole % (by weight of starting material) of Fe catalyst was charged to the reactor and the reaction sequence continued with samples being taken at various intervals. The results (area %) of such operation are set forth in the following Table A:

TABLE A

| Temperature: 200° C. Catalyst: 5 mole % Fe | | Pressure: Atmospheric | | | |
|---|---|---|---|---|---|
| Sample | Time (Hrs.) | *I | II | III | IV |
| 1 | 0 | 98.2 | — | — | — |
| 2 | 1 | 75.6 | 15.0 | 7.7 | .2 |
| 3 | 2 | 59.0 | 25.7 | 13.1 | .6 |
| 4 | 3.5 | 31.6 | 42.7 | 21.4 | 2.8 |
| 5 | 6 | 8.3 | 48.9 | 21.5 | 20.2 |
| 6 | 7 | 8.1 | 43.3 | 17.3 | 30.3 |
| 7 | 8 | 9.2 | 34.8 | 12.3 | 42.9 |
| 8 | 9 | 11.9 | 24.5 | 7.4 | 53.8 |
| 9 | 10 | 12.9 | 17.1 | 4.2 | 62.8 |
| 10 | 11 | 14.0 | 11.4 | 2.7 | 68.6 |
| 11 | 12 | 15.8 | 5.8 | 1.7 | 72.8 |
| 12 | 14 | 20.0 | .4 | 1.1 | 74.8 |
| 13 | 16 | 26.1 | .1 | .2 | 68.6 |

*G.C. peak for I coincides with peak for Product V, which begins to appear at about Sample No. 8.

The above example demonstrates the need for a catalyst and the effect thereof on the production of products (II)–(V) hereof.

EXAMPLE 2

In other operations utilizing the procedures of Example 1, Product II was utilized as a starting material to prepare products (IV) and (V). The reaction was conducted for 8 hours without a catalyst, and then for 8 hours with a catalyst added. The results are set forth in Table B:

TABLE B

| Temperature: 200° C. | | Pressure: Atmospheric | | |
|---|---|---|---|---|
| Sample | Time (Hrs.) | II | IV | V |
| 1 | 0 | 98.9 | — | .1 |
| 2 | 1 | 98.7 | — | .2 |
| 3 | 4 | 98.5 | — | .1 |
| 4 | *8 | 98.5 | — | .1 |
| **5 | 1.25 | 70.9 | 26.2 | 1.1 |
| 6 | 2 | 57.0 | 39.7 | 2.0 |
| 7 | 3 | 36.1 | 59.1 | 3.1 |
| 8 | 4 | 20.9 | 72.2 | 4.8 |
| 9 | 6 | .3 | 86.4 | 10.8 |
| 10 | 8 | — | 76.0 | 21.0 |

*5 mole % Fe added after first 8 hours.
**Time in Runs 5–10 is hours from point of catalyst addition.

The preceding Example 2 again demonstrates the need for a catalyst as well as the use of product (II) as a starting material to prepare products (IV) and (V). From the data set forth in Examples 1–2, it will be apparent to one skilled in the art that the reaction can be terminated whenever optimum amounts of one or more of the products is obtained and such product or products can thereafter be recovered by distillation, selective crystallization, etc. The process may be conducted in a batchwise manner, continuous, or a cyclic batch wherein the desired products are continuously or periodically removed leaving a quantity of the reaction mass in the reactor and adding makeup starting material and catalyst, or by distilling the product as it is removed leaving the catalyst in a distillation residue which can be recycled with makeup catalyst and reactant to the reactor. The continuous or cyclic processes can also be carried in a series of reactors if so desired.

The best mode for carrying out the most preferred embodiment of the invention presently known to the inventors is believed to be the chlorination of 2,4-dichloro-6-(trichloromethyl)pyridine at a temperature of from about 190° to about 220° C. in the presence of about 5 mole % $FeCl_3$ catalyst at atmospheric pressure although it is believed use of superatmospheric pressures may be advantageous in increasing the reaction rate.

The best mode contemplated for carrying out the invention on a continuous basis appears to comprise mixing a molten feed material (I) with an appropriate amount of an $FeCl_3$ catalyst and chlorinating the same in a reactor system comprising a series of four separate vented reactors lined with nickel, glass, etc. The reaction mass is pumped through each of the four reactors and is subjected to chlorination in each of the four reactors at a temperature of from about 190° to about 220° C. and a pressure of from about 190 to about 220 psig. The chlorine (in excess molar amounts) is sparged into the molten reaction mass in each reactor with the last of the reactors being preferably separately vented in order to maintain good control over the final product mix therein. The average residence time in the reactor system which will be necessary to achieve the desired end product can be readily determined by analyzing the end product of initial trials and accordingly adjusting the residence time of the reaction mass.

The product reaction mass exiting the reactor comprises the desired product(s) and by-products HCl, $Cl_2$, $CCl_4$, and by-product tars. The reaction mass is separated into its desired components by using conventionally available stripper and distillation techniques and equipment. In such operation, the reaction mass can be passed through one or more strippers to remove $CCl_4$, HCl and Cl₂. HCl can be injected into the stripper(s) to insure complete removal of Cl₂ before the reaction mass is passed through a vacuum distillation column, where the desired product can be recovered as overheads, with the still bottoms comprising catalyst, tars and some of the chlorinated pyridine products. A portion of the still bottoms can be recycled as part of the make-up feed used to mix with the starting material (I) in preparing the feed to the first reactor. The overhead stream can be subjected to one or more further vacuum distillation columns to obtain the desired product in the purity desired.

The Cl₂ pressure and temperature can be varied from one reactor to another if necessary to maintain the reaction in a steady state. While the sparging of the chlorine into the reaction mass provides agitation thereof, the reaction mass can also be stirred and agitation is preferably obtained by use of pump means to pass the reaction mass to each of the reactors. The best method contemplated for adding make-up catalyst to the molten recycle feed stream comprises adding iron powder to the molten feed (up to 10–15 wt. % iron based on the feed) and then chlorinating the mixture as soon as possible. The chlorination can be carried out with agitation at about 5–10 psig and at temperatures below about 150° C., preferably at or below about 100° C., until a homogeneous mixture is obtained. An exotherm normally results upon chlorination. For example, addition of about 0.2 mole/hr. of Cl₂ to a typical recycle stream at about 100° C. can cause an exotherm of about 30°–40° C. to increase the temperature to about 135°–140° C. A chlorination period of about 1.5–2 or more hours is usually required to obtain a homogeneous mixture, which can then be mixed in appropriate amounts with other recycle and fresh feed streams to form the desired starting material mixture.

Although the invention is described with respect to specific embodiments and modifications, the details hereof are not to be construed as limitations except to the extent indicated in the following claims.

What is claimed is:

1. A process for preparing chlorinated pyridine compounds which comprises contacting, in liquid phase, a starting material of the formula:

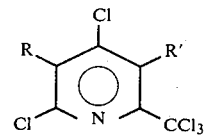

wherein R and R' each independently represent chloro or H, with the proviso that at least one of R and R' is always H, with chlorine at a temperature of at least about 160° C. to about 220° C. at superatmospheric pressures from about 190 psig to about 220 psig in the presence of a catalyst Lewis acid and amount thereof effective to catalyze the reaction, and thereafter recovering said chlorinated pyridine compounds.

2. The process of claim 1 wherein R and R' are each H and the chlorinated pyridine compounds are selected from the group consisting of 2,3,4-trichloro-,2,4,5-trichloro- and 2,3,4,5-tetrachloro-6-(trichloromethyl)pyridine and pentachloropyridine.

3. The process of claim 2 wherein 2,3,4-trichloro-6-(trichloromethyl)pyridine is the primary product obtained.

4. The process of claim 2 wherein 2,3,4,5-tetrachloro-6-(trichloromethyl)pyridine is the primary product obtained.

5. The process of claim 2 wherein pentachloropyridine is the primary product obtained.

6. The process of claim 1 wherein a mixture of the compounds of the formula is employed as the starting material.

7. The process of claim 1 wherein R' is H and R is chloro.

8. The process of claim 1 wherein R' is chloro and R is H.

9. The process of claim 1 wherein said process is carried out at a temperature of from about 190° to about 220° C., and pressures of from about 190 to about 220 psig in the presence of from about 1 to about 10 mole % catalyst.

10. The process of claim 2 wherein said process is carried out at a temperature of from about 190° to about 220° C., and pressures of from about 190 to about 220 psig in the presence of from about 1 to about 10 mole % catalyst.

11. The process of claim 1 wherein the catalyst is an iron or aluminum metal or halide thereof.

12. The process of claim 2 wherein the catalyst is an iron or aluminum metal or halide thereof.

13. The process of claim 11 wherein the catalyst is ferric chloride.

14. The process of claim 12 wherein the catalyst is ferric chloride.

* * * * *

UNITED STATES PATENT AND TRADEMARK OFFICE
CERTIFICATE OF CORRECTION

PATENT NO. : 4,227,001
DATED : October 7, 1980
INVENTOR(S) : Thomas J. Dietsche and Jim Love It is certified that error appears in the above—identified patent and that said Letters Patent is hereby corrected as shown below:

Column 2, line 29, "chloride" should be --chlorine--;

Column 4, line 30, last word in the sentence should be -- 2,3,4,5-tetrachloro-6-(tri- --;

Column 4, line 46, "one" should be -- another --;

Column 5, Table A, Sample 13, Column IV, the number should be -- 68.8 -- ;

Column 8, line 14, "Lewis acid" should come before "catalyst".

Signed and Sealed this

Twenty-fourth Day of March 1981

[SEAL]

Attest:

RENE D. TEGTMEYER

Attesting Officer    Acting Commissioner of Patents and Trademarks